United States Patent
Schoendube et al.

(10) Patent No.: US 11,112,346 B2
(45) Date of Patent: Sep. 7, 2021

(54) APPARATUS AND METHOD FOR DETECTING CELLS OR PARTICLES IN A FLUID CONTAINER

(71) Applicant: cytena GmbH, Freiburg (DE)

(72) Inventors: Jonas Schoendube, Freiburg (DE); Andre Gross, Freiburg (DE)

(73) Assignee: cytena GmbH, Freiburg (DE)

( * ) Notice: Subject to any disclaimer, the term of this patent is extended or adjusted under 35 U.S.C. 154(b) by 167 days.

(21) Appl. No.: 15/629,601

(22) Filed: Jun. 21, 2017

(65) Prior Publication Data

US 2017/0363534 A1     Dec. 21, 2017

(30) Foreign Application Priority Data

Jun. 21, 2016   (DE) .......................... 102016211038.1

(51) Int. Cl.
 *G01N 15/14*     (2006.01)
 *C12M 1/00*      (2006.01)
 (Continued)

(52) U.S. Cl.
 CPC ............ *G01N 15/1463* (2013.01); *B01L 3/02* (2013.01); *C12M 1/36* (2013.01); *C12M 41/36* (2013.01);
 (Continued)

(58) Field of Classification Search
 CPC ........... G01N 15/1463; G01N 15/1427; G01N 15/10; G01N 15/1468; G01N 2015/1006;
 (Continued)

(56) References Cited

U.S. PATENT DOCUMENTS

| 3,380,584 A | 4/1968 | Fulwyler |
| 4,667,830 A | 5/1987 | Nozaki et al. |

(Continued)

FOREIGN PATENT DOCUMENTS

| DE | 19706513 A1 | 8/1998 |
| EP | 0421406 A2 | 4/1991 |

(Continued)

OTHER PUBLICATIONS

Evans, Krista et al., "Assurance of Monoclonality in One round of Cloning Through Cell Sorting for Single Cell Deposition Coupled with High Resolution Cell Imaging", 2015, American Institute of Chemical Engineers, Biotechnol. Prog., vol. 00, No. 00; pp. 1-7.

(Continued)

*Primary Examiner* — Michelle F. Paguio Frising
*Assistant Examiner* — Trent R Clarke
(74) *Attorney, Agent, or Firm* — Michael A. Glenn; Perkins Coie LLP

(57) ABSTRACT

A apparatus for detecting cells or particles in a fluid container includes a dispenser configured to dispense at least one cell or at least one particle into a defined sub-volume of a fluid with which the fluid container is at least partially filled, and a detection apparatus configured to, in a time-coordinated manner with dispensing the at least one cell or the at least one particle by the dispenser, perform a detection in the defined sub-volume and/or in one or several sub-volumes underneath the defined sub-volume in order to sense the at least one cell or the at least one particle when entering the fluid or immediately after entering the fluid.

8 Claims, 5 Drawing Sheets

(51) Int. Cl.
*G01N 15/10* (2006.01)
*C12M 1/36* (2006.01)
*C12M 1/34* (2006.01)
*B01L 3/02* (2006.01)
*G01N 35/10* (2006.01)

(52) U.S. Cl.
CPC ............ *C12M 47/04* (2013.01); *G01N 15/10* (2013.01); *G01N 15/1427* (2013.01); *G01N 15/1468* (2013.01); *B01L 2200/025* (2013.01); *B01L 2300/0654* (2013.01); *B01L 2300/0858* (2013.01); *B01L 2300/168* (2013.01); *G01N 2015/1006* (2013.01); *G01N 2035/1034* (2013.01)

(58) Field of Classification Search
CPC ............... G01N 2035/1034; B01L 3/02; B01L 2200/025; B01L 2300/0654; B01L 2300/0858; B01L 2300/168; C12M 1/36; C12M 41/36; C12M 47/04
See application file for complete search history.

(56) References Cited

U.S. PATENT DOCUMENTS

| | | |
|---|---|---|
| 7,310,147 B2 | 12/2007 | Jiang |
| 7,646,482 B2 | 1/2010 | Jiang |
| 8,383,042 B2 | 2/2013 | Jiang |
| 8,417,011 B2 | 4/2013 | Klottrup et al. |
| 8,617,904 B2 | 12/2013 | Durack et al. |
| 8,795,981 B2 | 8/2014 | Burke et al. |
| 2008/0297774 A1 | 12/2008 | Jiang |
| 2008/0305969 A1 | 12/2008 | Dijksman et al. |
| 2009/0042200 A1 | 2/2009 | Okano et al. |
| 2015/0253223 A1 | 9/2015 | Foster et al. |

FOREIGN PATENT DOCUMENTS

| | | |
|---|---|---|
| EP | 1626278 A2 | 2/2006 |
| EP | 1686368 A2 | 8/2006 |
| EP | 2577254 B1 | 2/2015 |
| JP | 63116689 A | 5/1988 |
| JP | 2006081482 A | 3/2006 |
| JP | 5625125 B2 | 11/2014 |
| JP | 2015083922 A | 4/2015 |
| KR | 20130089619 A | 8/2013 |
| WO | 2011/154042 A1 | 12/2011 |
| WO | 2015173710 A2 | 11/2015 |
| WO | 2014057713 A1 | 9/2016 |

OTHER PUBLICATIONS

Tornay, Raphael et al., "Electrical Detection and Ejection of Beads in a One-Cell-Per-Drop Microdispenser", Microsystem Laboratory, EPFL-STI-LMIS, Lausanne, Switzerland; Conference Paper—Jul. 2007; 4 pages.

Selinummi, Jyrki et al., "Bright Field Microscopy as an Alternative to Whole Cell Fluorescence in Automated Analysis of Macrophage Images", PLoS ONE; www.plosone.org; Oct. 22, 2009; vol. 4; Issue 10; e7497.

Gross, Andrew et al., "Technologies for Single-Cell Isolation", International Journal of Molecular Sciences; ISSN 1422-0067; www.mdpi.com/journal/ijms; Jul. 24, 2015, 16897-16919.

"Slow motion water drop splash", Istockphoto, Mar. 5, 2014 (Mar. 5, 2014), p. 1 pp., XP054978736, Retrieved from the Internet: URL:https://www.istockphoto.com/nl/video/slow-motion-water-dropsplashgm477073369-35910430 [retrieved Oct. 2, 2018] (pdf not available).

APPARATUS AND METHOD FOR DETECTING CELLS OR PARTICLES IN A FLUID CONTAINER

CROSS-REFERENCE TO RELATED APPLICATIONS

This application claims priority from German Patent Application No. 102016211038.1, which was filed on Jun. 21, 2016, which is incorporated herein in its entirety by this reference thereto.

BACKGROUND OF THE INVENTION

The present invention concerns apparatuses and methods for detecting cells or particles dispensed by a dispenser into a defined sub-volume of a fluid located in a fluid container.

After inserting cells or particles into a fluid container, sensing if the cell or the particle is actually located in the fluid container is generally often performed. For example, monoclonal antibodies and other proteins, which are subsequently called products, are prepared by means of so-called monoclonal cell lines. These are populations of cells originating from a single cell. This ensures to the best extent that all cells of the population comprise approximately the same genotype and, thus, generate a product which is as equal as possible.

In order to generate a monoclonal cell line, cells are individually transferred into so-called microtiter plates and multiply there in a controlled manner until the desired population size is reached. Depositing single cells in the microtiter plates occurs by free-jet printing methods or by pipetting single cells into the single bowls or cavities of the microtiter plate, which are herein after referred to as "wells". These wells represent containers. When manufacturing therapeutic products from cell cultures, it has to be demonstrated for regulatory reasons that indeed only one cell was located in the well at the beginning of the process. It is important for the well bottom to be sufficiently large, i.e., significantly larger than a cell, in order to allow the population to grow to the useful size. Ultimately, from a series of a few hundreds to thousands of such clone populations, the one that produces the desired product in the most stable manner and in the greatest quantity is transferred to manufacturing.

Methods for sensing cells in fluid containers, for example, the wells of a microtiter plate, are known from the conventional technology.

In "Assurance of monoclonality in one round of cloning through cell sorting for single cell deposition coupled with high resolution cell imaging", 2015, American Institute of Chemical Engineers, Biotechnol. Prog., vol. 00, No. 00, http://doi.org/10.1002/btpr.2145, K. Evans et al describe a process for producing monoclonal cell lines. Cells are transferred into the well of a microtiter plate by means of a so-called FACS apparatus (FACS=fluorescent activated cell sorting). After that, the same is centrifuged in order to transport the cells to the bottom. Successively, the entire well bottom is examined under the microscope, typically by means of a so-called imager, and single cells are searched for therein, which is effected by the user. In this case, it is extremely difficult to recognize a single cell in the large observation volume.

Flow cytometry represents a known method for analyzing cells passing an electric voltage or a light ray. For example, U.S. Pat. No. 3,380,584 A describes a method for separating particles in which a printing method comprising a continuous jet is employed, which has the disadvantage of drops being continuously generated without being able to interrupt the drop stream in a controlled manner. In selectively sorting cells or particles by means of this technique, the drops are therefore deposited at different positions according to content. This occurs by an electrostatic deflection during flight. The higher the number of positions and the involved deposition accuracy (e.g., in 96 or 384 well plates), the more difficult and technically complex the process. From EP 0 421 406 A2, apparatuses and methods for separating particles are known, in which a thermal printing head is used in order to dispense particles. The particles are arbitrarily arranged in the reservoir and are optically analyzed after ejection during flight. The above-described methods allow for depositing cells individually but cannot achieve an efficiency of 100 percent. Therefore, the microtiter plates have to be examined under the microscope afterwards by means of so-called imagers.

From U.S. Pat. No. 7,310,147 B2, EP 1 686 368 A2, U.S. Pat. No. 8,417,011 B2 and U.S. Pat. No. 8,795,981 B2, apparatuses and methods for sensing cells and particles in microtiter plates are known.

U.S. Pat. No. 7,646,482 B2 describes a method for automatically finding the right focal plane in order to, e.g., examine cells at a well bottom under a microscope. In the course of this, the method detects patterns in the sensor signal, while the microscope focuses through the bottom of the plate.

U.S. Pat. No. 8,383,042 B2 describes an imager comprising a vacuum holder. The vacuum holder sucks in the microtiter plate in order to maintain the bottom of the microtiter plate in a plane manner and, in this way, provides a lower variance of the distance of the well bottom to the objective.

From WO 2011/154042 A1, apparatuses and methods for dispensing a cell or a particle in a free-flying droplet are known The inventors have realized that current dispensing methods for individually depositing may detect and deposit cells with high efficiency, while not being 100% reliable.

SUMMARY

According to an embodiment, an apparatus for detecting cells or particles in a fluid container may have: a dispenser configured to dispense at least one cell or at least one particle into a defined sub-volume of a fluid with which the fluid container is at least partially filled; a detection apparatus configured to, in a time-coordinated manner with dispensing the at least one cell or the at least one particle by the dispenser, perform a detection in the defined sub-volume and/or in one or several sub-volumes underneath the defined sub-volume in order to sense the at least one cell or the at least one particle when entering the fluid or immediately after entering the fluid.

According to another embodiment, a method for detecting cells or particles in a fluid container may have the steps of: dispensing at least one cell or at least one particle into a defined sub-volume of a fluid with which a fluid container is at least partially filled; performing, in a time-coordinated manner with dispensing the at least one cell or the at least one particle, a detection in the defined sub-volume and/or in one or several sub-volumes underneath the defined sub-volume in order to sense the at least one cell or the at least one particle when entering the fluid or immediately after entering the fluid.

Embodiments of the invention provide an apparatus for detecting cells or particles in a fluid container, comprising:

a dispenser configured to dispense at least one cell or at least one particle into a defined sub-volume of a fluid with which the fluid container is at least partially filled;

a detection apparatus configured to, in a time-coordinated manner with dispensing the at least one cell or the at least one particle by the dispenser, perform a detection in the defined sub-volume and/or in one or several sub-volumes underneath the defined sub-volume in order to sense the at least one cell or the at least one particle when entering the fluid or immediately after entering the fluid.

Embodiments of the invention provide a method for detecting cells or particles in a fluid container, comprising:

dispensing at least one cell or at least one particle into a defined sub-volume of a fluid with which a fluid container is at least partially filled; and performing, in a time-coordinated manner with dispensing the at least one cell or the at least one particle, a detection in the defined sub-volume and/or in one or several sub-volumes underneath the defined sub-volume in order to sense the at least one cell or the at least one particle when entering the fluid or immediately after entering the fluid.

In embodiments of the invention, the object, i.e., the cell or the particle, such as the single cell or the single particle, is neither detected in the dispenser nor in a free-flying drop in which the object is dispensed. Thus, in embodiments, the detection does not occur during transport, e.g., into the well of a microtiter plate. Rather, the cell or the particle is sensed when entering the fluid or immediately after entering the fluid which at least partially fills the fluid container in which the cell or the particle is to be sensed. Thus, embodiments allow for a reliable verification that the cell or the particle has ended up in the fluid container and is actually located in the fluid container. In embodiments, the dispenser dispenses a free-flying drop in which the object, i.e., the cell or the particle, is encapsulated so that a reliable verification that the drop has actually landed in the fluid container, e.g., a well of a microtiter plate, is possible in such embodiments.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
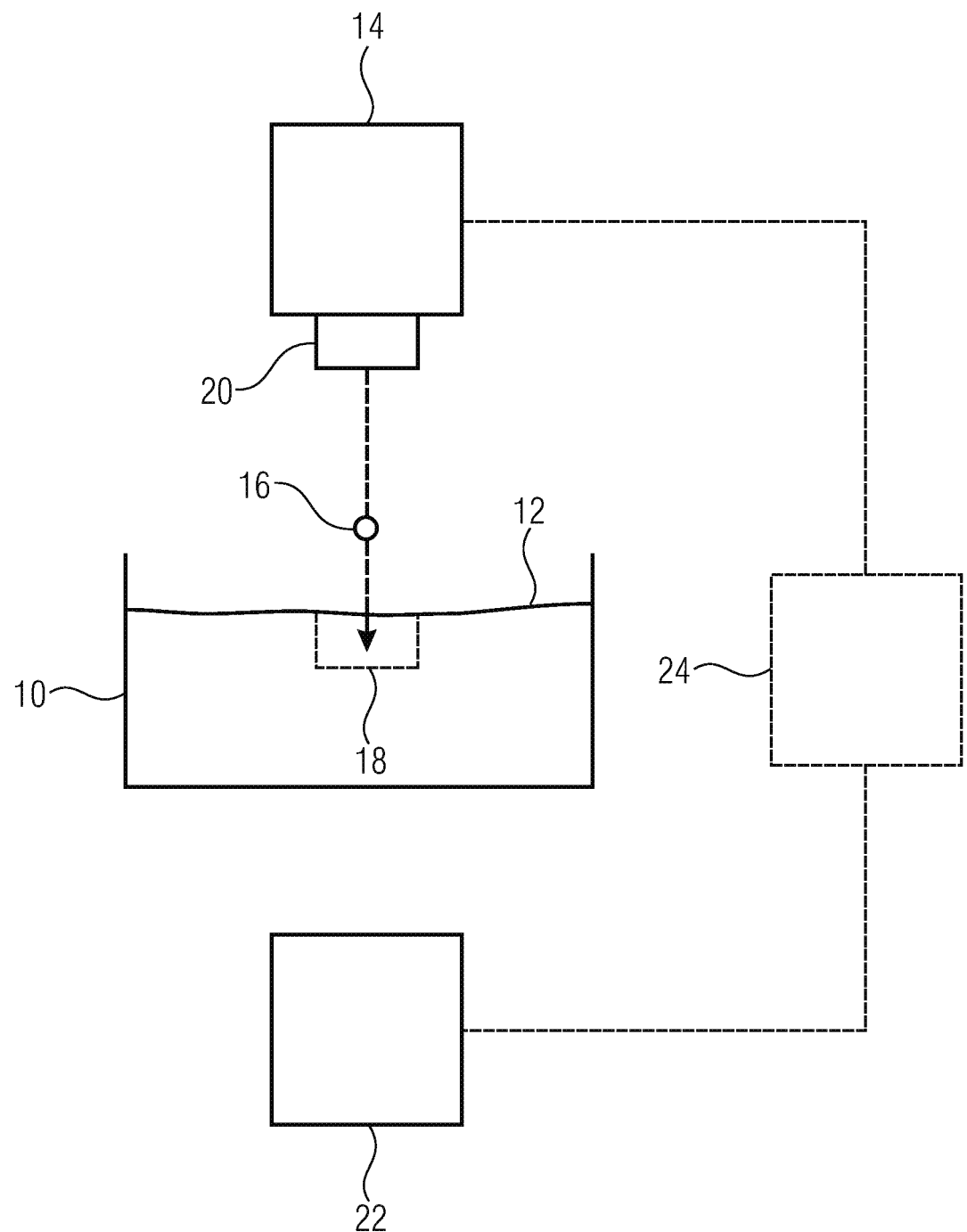
FIG. 1 shows a schematic illustration of an apparatus for detecting cells or particles in a fluid container.

Before the embodiments are described successively, it is to be noted that the invention is not restricted by these special embodiments, but by the wording of the claims.

Furthermore, at first, some of the terms used herein are described. A dispenser is understood to be an apparatus configured for dispensing cells or particles. Examples of dispensers may be drop generators configured for dispensing liquid quantities in the form of free-flying drops. A drop-on-demand printing technology is understood to be a printing technology enabling selectively generating single drops from a nozzle at a chosen point in time. In contrast, a continuous-jet printing technology is understood to be a printing technology in which a thin continuous liquid jet is dispensed from a nozzle in a pressure-driven manner. By applying a high-frequency oscillation at the nozzle, after discharge, the jet disintegrates into single drops which may be deflected electrostatically, inter alia. An observation volume is understood to be a volume area of a specific height, in which measurements or observations are made. Observation volumes may be arranged in a defined two-dimensional grid of a certain height. A microtiter plate is understood to be a plate containing several mutually insulated cavities (wells) in rows and columns. Often, microtiter plates are rectangular and usually consist of plastic. An imager is understood to be an imaging apparatus such as an automatic microscope which, e.g., enables examining entire microtiter plates under a microscope. In this case, imagers are configured to individually photograph each well of the microtiter plate in high resolution. Successively, this enables the user to find single cells in the wells.

As explained above, known systems lack the verification that a dispensed drop comprising a cell or a particle has actually landed in the well of a microtiter plate. For this purpose, a secondary technology such as an imager has generally been used. Accordingly, the user later does not know if the desired single cell has actually reached the well as long as she/he is solely using the dispensing system.

Further, it was also realized that there are more problems in using imagers. The area to be photographed by the imager is huge when compared to a cell, by a factor of approximately 1:1,000,000. In order to ensure that only one cell is in the well, the entire well area has to be scanned. At the same time, the resolution has to be high enough that the cell may be reliably identified as such. The higher the resolution, the smaller the image field, the longer scanning takes. Further, scanning may involve capturing several images in a spatially offset manner and combining these to an overall image. If the cell is located exactly between two such images, cut-off or, in the worst case, disappearance of the illustration of the cell may occur due to combining. Furthermore, the optical focal depth is limited due to the high optical resolution. If the system is not precisely focused, cells are blurred and, in the worst case, may be overlooked. The scan of the entire well volume, i.e., all focal planes from the bottom to the surface of the liquid, is expensive with regard to time and data consumption and, thus, hardly feasible. Using current imager technology, it would take approximately ten hours to scan a 96 well plate. The resulting data volume would be about 40 GB. Based on the amount of plates and the time the data would have to be stored, this would not be possible. Furthermore, the cells are transported to the focal plane i.e., to the well bottom, before the scan. Typically, this is achieved by centrifugation after the cell deposition. For this purpose, the plates are centrifuged at high centrifugal forces until the cells are located at the bottom. Due to the occurrence of radial centrifugal forces during acceleration and deceleration, cells may be transported to the outside. They then often come to rest in the corners of the wells. There, they are very difficult to identify. Microtiter plates are subject to manufacturing tolerances despite extensive standardization. The height of the well bottom may vary both in the total and from well to well.

This causes the level in which the cells lie and, thus, the focus to not be uniform. A wrong focus may smear the objects towards the edge.

Due to the way the microtiter plates are produced by injection molding or deep drawing, the wells usually comprise demolding edges and the corners at the bottom are not 90° but slightly round. This results in strong diffraction and shading effects in the imager. Thus, cells which come to rest in the corners may possibly not be identified unambiguously or at all. If the well bottom becomes higher towards the edge, cells are only in focus in the center and out of focus on the outside. Furthermore, single cells may be depicted twice due to refraction effects. A so-called ghost image of the cell may arise in the immediate vicinity of the actual image. Thus, however, it cannot be reliably determined whether this is a ghost image or actually a second cell.

Figure 6:
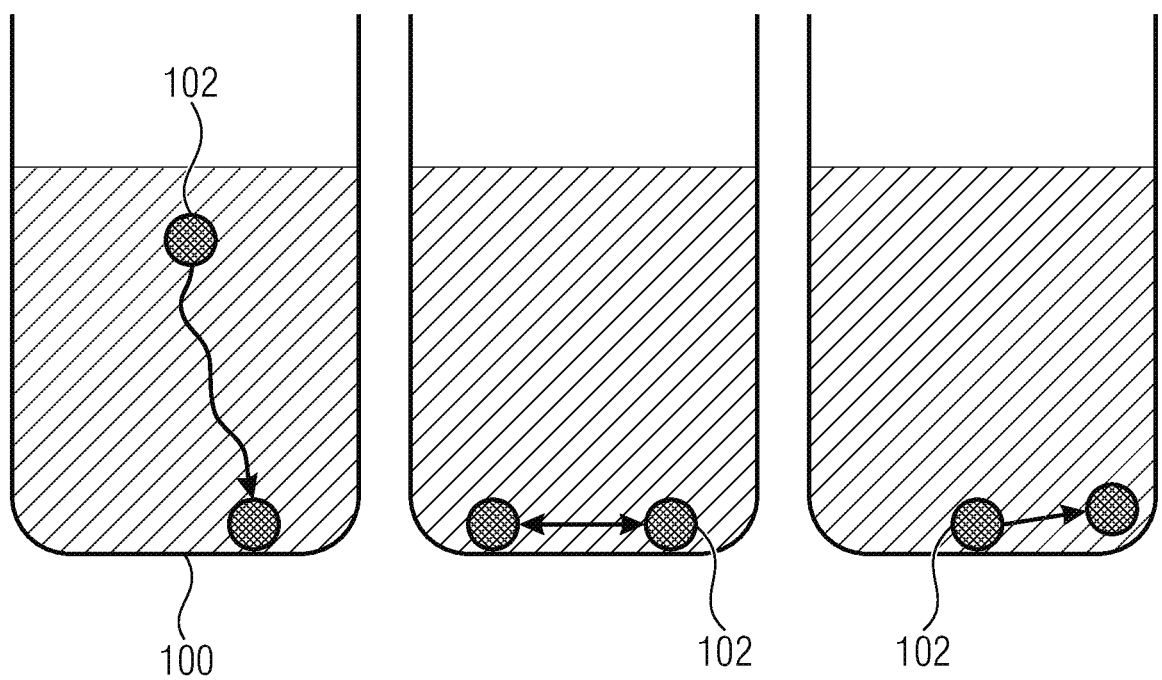
FIG. 6 shows schematic illustrations of fluid containers for explaining problems occurring in known methods.

As described above, the microtiter plates are usually brought from a dispensing system to an imager system in order to check if cells or particles are arranged in the wells of the microtiter plates. By means of the steps of centrifuging and changing the microtiter plates between apparatuses, as well as by means of the passing time between depositing the cell by dispensing and sensing in the well, the cells in the well may practically come to rest anywhere at the bottom of the well. On the left-hand side, FIG. 6 shows a fluid container 100 in which a cell 102 has sunk to the bottom of the fluid container 100, e.g., the well of the microtiter plate, by settling due to time passed. The illustration in the middle of FIG. 6 shows a movement of the cell 102 on the bottom by a transport. The illustration on the right side of FIG. 6 shows a movement of the cell 102 by means of centrifugal forces as they may occur due to centrifuging, for example. These observations show that the cells in the well may practically come to rest anywhere on the bottom, while they actually often come to rest in the corners.

Switching to other substrates comprising a smaller well bottom area would theoretically solve some problems such as combining the images. However, this has other drawbacks. The ratio between a planar surface of the well bottom to the non-planar edge region, in which shading and defocusing occur, would shift into the negative. The probability of a cell coming to rest at the edge would increase. The area at the well bottom or, above all, the volume of the well available to the cells for growing would be significantly smaller. Cells would grow worse and could not form sufficiently large populations. This would cause the entire work process to be more complex. Due to the small well volume, the medium would have to be exchanged or filled in order to supply the cells with nutrients for a sufficiently long period of time. The risk of cross-contamination or the probability of premature death of the population would increase.

Thus, the inventors have realized that a dispensing technology alone is not sufficient for the verification of a single cell in a fluid container such as a well of a microtiter plate. Furthermore, due to the above-described problems, imagers are also limited in their significance in this case. Ultimately, this may lead to the fact that the optimal population selected for the production cannot reliably be identified as monoclonal and, thus, has to be discarded. This leads to high economic risks and high costs.

Embodiments of the invention provide apparatuses and methods solving the above-described problems and enabling a reliable detection even of single cells or particles in a fluid container.

In FIG. 1, an embodiment of an apparatus for detecting cells or particles is shown. The apparatus includes a fluid container 10. For example, the fluid container may be a well (cavity) of a microtiter plate comprising an array of corresponding wells. The fluid container may comprise a bottom and side walls limiting a volume of the fluid container and enabling the fluid container to be at least partially fillable with a fluid. In embodiments, the fluid container 10 consists of a transparent material. The fluid container 10 is at least partially filled with a fluid 12 such as a liquid. For example, the liquid may be a nutrient solution for a cell culture. In the following, reference is made to a liquid 12. The apparatus further comprises a dispenser 14 configured to dispense at least one cell or particle 16 into a defined sub-volume 18 of the liquid 12. The dispenser 14 may be a drop-on-demand dispenser configured to dispense a single drop, in which a cell or a particle is encapsulated, from a nozzle 22. The dispenser 14 is positioned or may be positioned relative to the fluid container 10 such that the cell or the particle is dispensed into the defined sub-volume 18. Accordingly, the dispenser may be configured to dispense single drops from a cell suspension or particle suspension, and may comprise a structure as described in WO 2011/154042 A1, for example.

The apparatus further comprises a detection apparatus 22 configured to, in a time-coordinated manner with dispensing the at least one cell 16 (or the at least one particle) by the dispenser 14, perform a detection in the defined sub-volume 18 and/or in one or several sub-volumes underneath the defined sub-volume in order to sense the at least one cell 16 when entering the fluid 12 or immediately after entering the fluid 12.

In examples, the fluid container is part of the apparatus. In examples, the fluid container is not part of the apparatus and may be provided separately from the apparatus.

Figure 3:
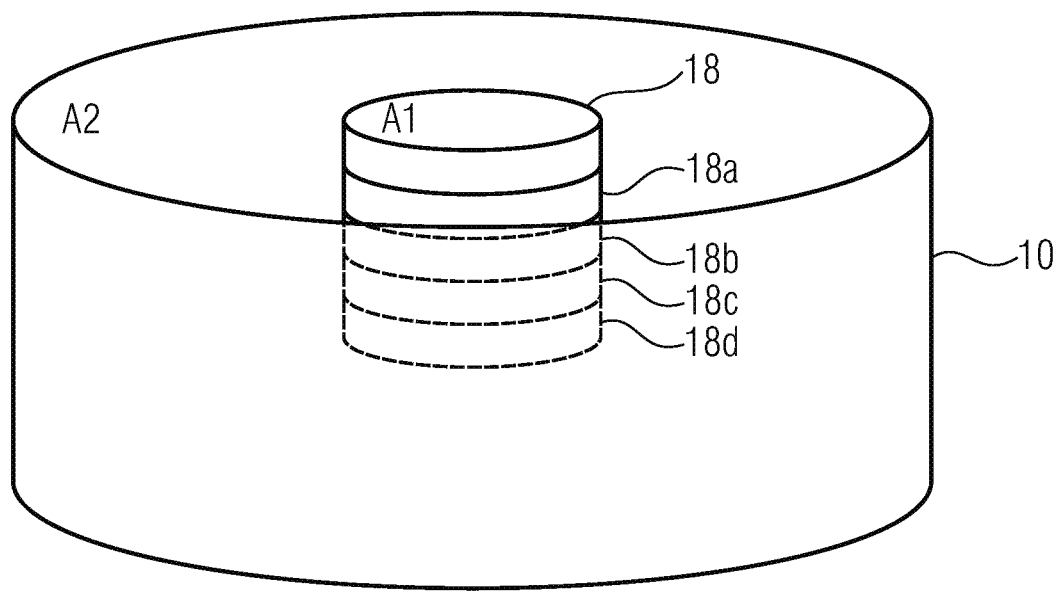
FIG. 3 shows a schematic illustration of a fluid container.

With regard to the explanation of the defined sub-volume and the one or several sub-volumes arranged underneath the defined sub-volume, reference is made to FIG. 3, which shows a schematic perspective view of the fluid container 10. In FIG. 3, the sub-volumes are illustrated as slices, the defined sub-volume 18 being formed by the uppermost slice. For example, the defined sub-volume 18 may extend downwards by a predetermined depth from the liquid surface of the liquid arranged in the fluid container 10. The depth of each sub-volume may correspond to the depth of focus of a focal plane of the detection apparatus. For example, the same may be in the range of 40 μm to 60 μm. In the illustration in FIG. 3, for reasons of simplification, it is assumed that the liquid completely fills the container 10. In reality, the container will usually only be partially filled with the liquid. As can be seen in FIG. 3, the area A1 of the defined sub-volume 18 is significantly smaller than the area A2 of the fluid container 10. Here, area is understood to be the area parallel to the liquid surface. The one or several sub-volumes underneath the defined sub-volume 18 are arranged underneath the sub-volume 18 with increasing depth. The sub-volumes may overlap in a direction perpendicular to the liquid surface. The sub-volumes 18 and 18a-18d may each be configured such that a detection by the detection apparatus 22 may occur in the entire sub-volume. For example, the sub-volumes are dimensioned such that an imaging sensor may generate a focused image of the respective sub-volume.

The dispenser 14 and the detection apparatus 22 may be connected with a control 24 which coordinates dispensing the cell or the particle by the dispenser and detecting by the detection apparatus 22 in a timely manner. In embodiments, the control may be arranged in the dispenser or the detection apparatus. As is obvious to those skilled in the art, the control may be implemented by, e.g., an accordingly programmed computing means or by a user specific integrated circuit. In embodiments, the detection apparatus may be configured to sense the at least one cell or the at least one particle no later than ten seconds after entering the fluid, i.e., the fluid 12 in the embodiment shown. For example, the detection apparatus may be configured to perform detection in one of the sub-volumes when it is expected that the cell or the particle is located in the sub-volume. If the detection occurs in the sub-volume 18 arranged directly below the surface of the liquid 12, sensing may occur immediately after dispensing by the dispenser, e.g., in one second or in an even shorter period of time. In embodiments of the invention, the detection apparatus is configured to sense the cell or the particle in a sub-volume arranged above the bottom of the fluid container. Thus, the object may be sensed before it has reached the bottom of the fluid container.

Figure 2:
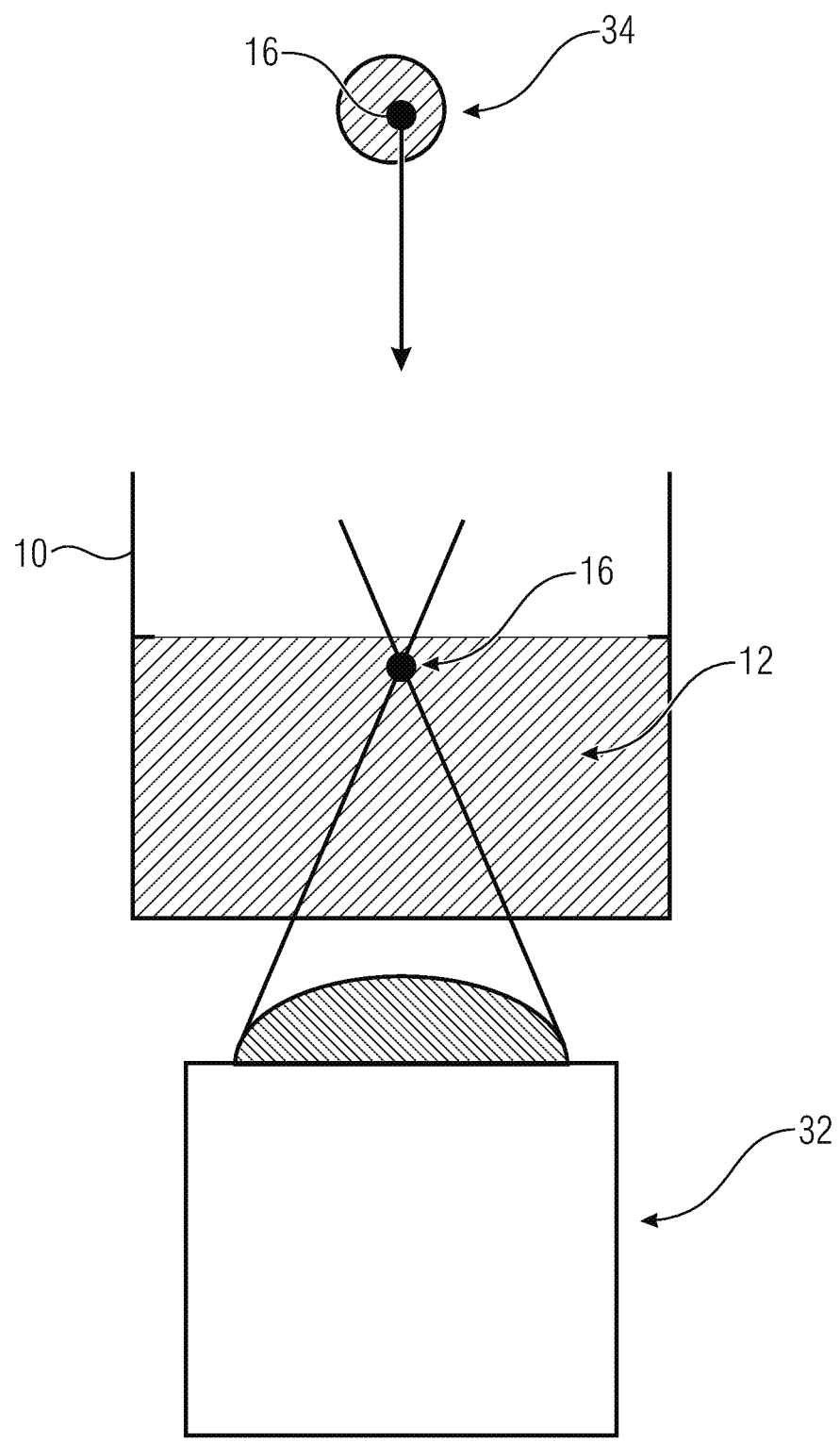
FIG. 2 shows a schematic illustration of an apparatus comprising an optical sensor.

FIG. 2 shows an embodiment of an apparatus for detecting cells or particles, wherein the detection apparatus comprises an optical sensor 32. A dispenser (not shown in FIG. 2) is configured for dispensing drops 34 of a cell suspension, a cell 16 being arranged in the drop 34. The dispenser dispenses the drop into the fluid container 10, e.g., in the form of a well of a microtiter plate, which is prefilled with a cell medium 12. In embodiments, the shape of the fluid container may be selected such that the surface of the fluid is flat. An optical sensor 32 such as a microscope comprising an adjustable focus is located below the transparent fluid container 10. A cell/a particle is already captured with the optical sensor when entering the fluid in the fluid container 10. The optical sensor comprises a camera and optics. The optical sensor 32 focuses on the system through the transparent fluid container. For this, the optical sensor 32 representing an image capturing apparatus focuses on a defined sub-volume directly underneath the surface of the liquid 12. For example, the optical sensor 32 may focus on a sub-volume directly underneath the liquid surface or on a sub-volume in a depth of less than 5 mm from the surface of the liquid 12. The aim is to verify that the cell/the particle actually lands in the reservoir. It is not necessary to wait until the cell/the particle has sunk to the bottom of the reservoir. In the described sensing, it is not important where on the bottom of the fluid container the cell/the particle finally comes to rest.

In embodiments, single drops of a cell suspension or a particle suspension each comprising a volume of approximately 200 pl may be dispensed into a well of a microtiter plate. For example, the well may be filled up to half with a liquid beforehand, while the focus of the optical sensor may be constantly held underneath the liquid surface. Thus, the cell/the particle may settle through the focal plane of the optical sensor 32, which may be a light microscope. Capturing an image in a time-coordinated manner with dispensing the cell/the particle allows for a reliable detection of the cell/the particle in the fluid container. Furthermore, in embodiments, an image series of the defined sub-volume (or several defined sub-volumes) may be captured in order to allow for an even more reliable detection of the cell/the particle. Practical experiments have shown that by using such a structure it is easily possible to recognize that the object (the cell/the particle) in the observation volume (the defined sub-volume) penetrates the liquid and, successively, settles towards the bottom, wherein the same may be observed by the optical sensor.

In alternative embodiments, the focal plane of the optical sensor may be moved against the settling movement of the object in order to reduce the time until detection. In other words, the detection apparatus may be configured to, starting with a sub-volume in a greater depth, successively perform detections in several sub-volumes of a respectively decreasing depth.

Performing several detections, e.g., by an image capturing apparatus, enables that the object is exactly in focus during performing the at least one detection and, thus, may be absolutely reliably detected. Practical experiments have shown that, e.g., a polystyrene particle comprising a diameter of 15 µm may be easily sensed by means of a corresponding procedure.

For example, several sub-volumes comprising a respectively decreasing depth are shown in FIG. 3 of the present application and are provided with the reference numerals 18a-18d. For example, a detection could immediately be started in the sub-volume 18d after dispensing the drop by the dispenser and detections could be successively performed in sub-volumes comprising a respectively decreasing depth, i.e., from 18c to 18b to 18a to 18. Due to this, it is possible to sense with a high reliability a cell or a particle brought into the liquid 12 in the fluid container 10.

In alternative embodiments, the detection apparatus could also be configured to, starting with a sub-volume in a lesser depth, successively perform detections in several sub-volumes comprising a respectively increasing depth.

In embodiments of the invention, the defined sub-volume may comprise an area of less than 10 mm$^2$. For example, the sub-volume may comprise an area of 2×2 mm at a depth corresponding to the depth of focus of a focal plane of the detection apparatus. In embodiments, the detection apparatus may be configured to capture an image sequence in a sub-volume until the cell or the particle settles into the sub-volume. In embodiments, the detection apparatus may be configured to focus on a sub-volume arranged directly underneath the liquid surface, or on a sub-volume arranged in a depth of less than 5 mm below the liquid surface. In embodiments of the invention, the detection apparatus may be configured to perform several detections of the respective sub-volume, e.g., with a capturing rate between 50 Hz and 150 Hz, e.g., 100 Hz. In embodiments, the detection apparatus may be an image capturing apparatus with an image capturing rate of 100 Hz. In embodiments, the focus of the image capturing apparatus may be traversed in order to perform a vertical scan in a limited lateral region. In embodiments, for example, a traverse speed may be 5 mm/s while images are captured in order to capture images at different depths. In embodiments, for example, the volume of the liquid in the fluid container may be 150 µl, which is a typical volume in a cell culture.

Embodiments may be used in dispensing a documented number of particles. In particular, embodiments of the invention may be used in a cell line production in order to dispense single cells into cavities of a microtiter plate in a reliable and documented manner. In embodiments of the invention, single cells or a particular number of cells may be printed in monoclonal cell cultures to verify the monoclonality and for further processing. In particular, embodiments may be used for single cell analysis.

Figure 4:
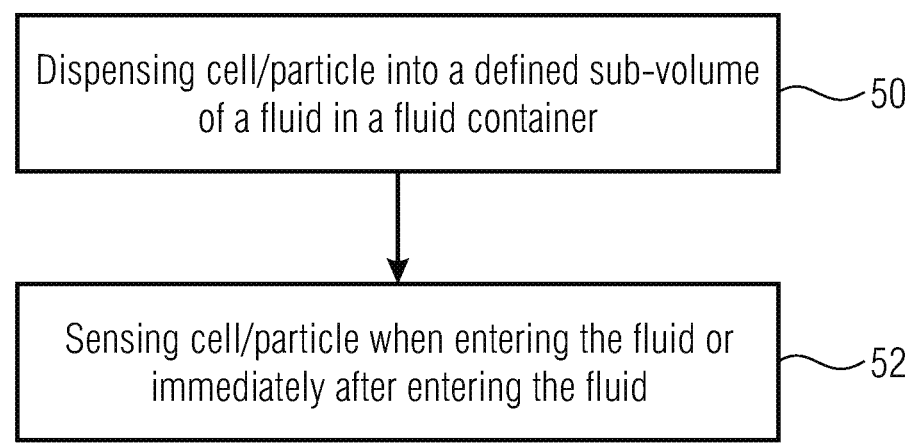
FIG. 4 shows a flowchart of an embodiment of a method for detecting cells or particles in a fluid container.

Hence, embodiments of the invention provide a method in which an object, i.e., a cell or a particle, is dispensed into a defined sub-volume of a fluid with which a fluid container is at least partially filled, step 50 in FIG. 4. The object is sensed when entering the fluid or immediately after entering the fluid. For this, one or several detections may be performed in the defined sub-volume and/or in one or several sub-volumes underneath the defined sub-volume in a time-coordinated manner with dispensing the at least one cell or the at least one particle, step 52 in FIG. 4. Sensing the object may occur no later than ten seconds after entering the fluid, advantageously, no later than five seconds and more advantageously, no later than one second after entering the fluid. In embodiments, the defined sub-volume comprises an area which is smaller than the area of an entry opening of the fluid container. In embodiments, the object is dispensed onto a surface of the fluid. In embodiments, the object is dispensed into a defined fluid volume underneath the surface of the liquid.

In embodiments, the dispenser is configured to transfer particle suspension or cell suspension selectively into the fluid container at a predefined position. Possible mechanisms for this are: drop-on-demand printing (in a piezoelectric or thermally driven manner), a fluorescence-based flow symmetry (FACS—fluorescence activated cell sorting), pipetting (manually or by means of a pipetting robot), a dosing apparatus (valve-based, by means of a displacer, by means of a syringe pump, etc.) or a micro-manipulator. In embodiments, the detection apparatus is configured to focus on the upper edge of the liquid level in the center of the fluid container (reservoir). With this, the region of the impact of the drop, i.e., of the transport volume comprising the object therein, may automatically be in focus. Alternatively, as described above, the liquid volume in the center of the fluid container may be focused through starting from below as soon as the drop has been dispensed by the dispenser. This ensures that the object is in focus at a random point in time. For this purpose, it is not necessary to know the exact filling level of the fluid container in order to find the focus.

In order to keep the meniscus of the liquid in the reservoir as flat as possible and to, thus, have a reproducible liquid level in the fluid container, reservoirs comprising special shapes may be used, e.g., as described in EP 1 880 764 B1. For example, flat steps are excellently suitable for drawing the meniscus flat when the fluid container is filled with a precisely known liquid volume.

In embodiments of the invention, the object may be applied to the surface of a fluid in the fluid container or be inserted underneath the surface into the fluid. In embodiments, the detection occurs by means of an image capturing apparatus focusing on a corresponding sub-volume. In alternative embodiments, different detection apparatuses may be used. For example, a detection apparatus may be implemented by electrodes formed in the wall of the fluid container, which are configured to sense a capacity between the same. For example, several such electrodes may be arranged in different depths of the fluid container in order to perform detection in several different depths.

Hence, embodiments of the invention provide apparatuses and methods in which an observation volume smaller than the container volume is observed in the fluid container (reservoir). In embodiments, solely the entry point of the object into the fluid or the liquid is observed. Accordingly, a sensor for observing the observation volume and a mechanism for selectively dispensing particles solely into the observation volume may be provided. Accordingly, apparatuses and methods for recognizing particles and cells in a liquid comprise a reservoir or a cavity for receiving liquids, a mechanism for transferring liquids with one or several cells/particles and a sensor for recognizing single or several particles or cells. In embodiments, the reservoir is a reservoir for receiving particle suspensions or cell suspensions, the mechanism is a mechanism for selectively transferring the particle suspension or cell suspension into the reservoir at a predefined position, and the sensor is a sensor for recognizing single or several particles or cells in a cell medium at the predefined position.

According to embodiments, the sensor may be an optical sensor or an imaging sensor. The imaging sensor may comprise an adjustable focus and may be configured to focus through the observation volume. In other words, the imaging sensor may be configured to vertically scan the observation volume. In embodiments, this occurs from underneath the fluid container so that an adjustment of the focus occurs in a depth direction. In embodiments, transferring a particle suspension or cell suspension into the fluid in the fluid container occurs without contact in the form of free-flying drops. In embodiments, the free-flying drop comprises a volume of a maximum of 100 nl. In embodiments, the fluid container is prefilled with a liquid. In embodiments, the liquid with the cell/the particle is inserted into the fluid container. In embodiments, the fluid container is configured such that a liquid located therein comprises a flat surface (meniscus). In embodiments, for this, the fluid container comprises an edge of a particular depth, the volume of the liquid in the fluid container being adapted such that the liquid reaches up to the edge. In embodiments, the fluid container comprises a volume of at least 100 µl.

In embodiments, a mechanism is provided by which the fluid container, the dispenser and the detection apparatus may be traversed towards each other in order to subsequently insert cells/particles into several fluid containers, e.g., into the wells of a microtiter plate. For example, such a mechanism may be configured to move the several fluid containers, e.g., the microtiter plate, relative to the dispenser and the detection apparatus or to move the dispenser and the detection apparatus relative to the several fluid containers. Thus, it is possible to subsequently insert cells/particles into several fluid containers and immediately reliably sense if a cell/particle has ended up in each of the fluid containers.

The technique described herein provides significant advantages over known methods.

A significant drawback of known dispensing technologies in combination with imagers is the time and the process steps between dispensing, i.e., the cell transport into the fluid container (the well), and imaging the well. Here, a single cell was first deposited in a well of the microtiter plate, the microtiter plate was then removed from the dispenser, the plate was then centrifuged, the plate was then inserted into an imager and sensing by the imager then occurred. In addition, there are also the bad conditions in imaging the well bottom due to the manufacturing-related geometries of the wells. These drawbacks are compensated by the technique described herein. Sensing occurs directly with depositing the cell, i.e., dispensing. Depositing may be performed in a highly precise manner so that the cell reaches the well at a predefined position, e.g., centrally, and the same may already be scanned directly at the entry point of the liquid in the well. By this, the plate does not have to be moved and/or the cells do need not be centrifuged to the well bottom. By this, the steps of removing the plate from the dispenser, centrifuging the plate and inserting the plate into the imager may be omitted. Furthermore, sensing (scanning) may solely occur from the bottom up using a focus shift at the location of entry of the cell into the fluid container (the well). This may occur very quickly and the cell may automatically be in the image.

Therefore, embodiments of the present invention are advantageous in that dispensing and detecting occur directly in succession and moving the plate and therefore moving the cell in the container in an uncontrollable manner do not occur. There are no intermediate steps between dispensing and detecting. Furthermore, sensing occurs in the free liquid and not at the well bottom. Therefore, there are no shading effects or refraction effects and no ghost images of cells. Furthermore, other drawbacks may be avoided which may impair sensing at the well bottom, e.g., scratches, finger prints (bottom/outside), (electrostatically) attracted dust (bottom/outside) or dirt (debris) from above/inside, which, e.g., was centrifuged to the well bottom with the cell. In embodiments of the invention, vertical scanning is used instead of horizontal scanning so that focus problems and a necessity to combine images do not exist. The volume to be scanned is substantially smaller than the entire well volume. In contrast to horizontal scanning, traversing the plate is omitted, which in turn allows for faster sensing. Finally, the image quality does not anymore depend on the quality of the fluid container, e.g., the microtiter plate substrates or their bottoms, since sensing occurs while the cell/the particle is located in the free liquid.

Figure 5:
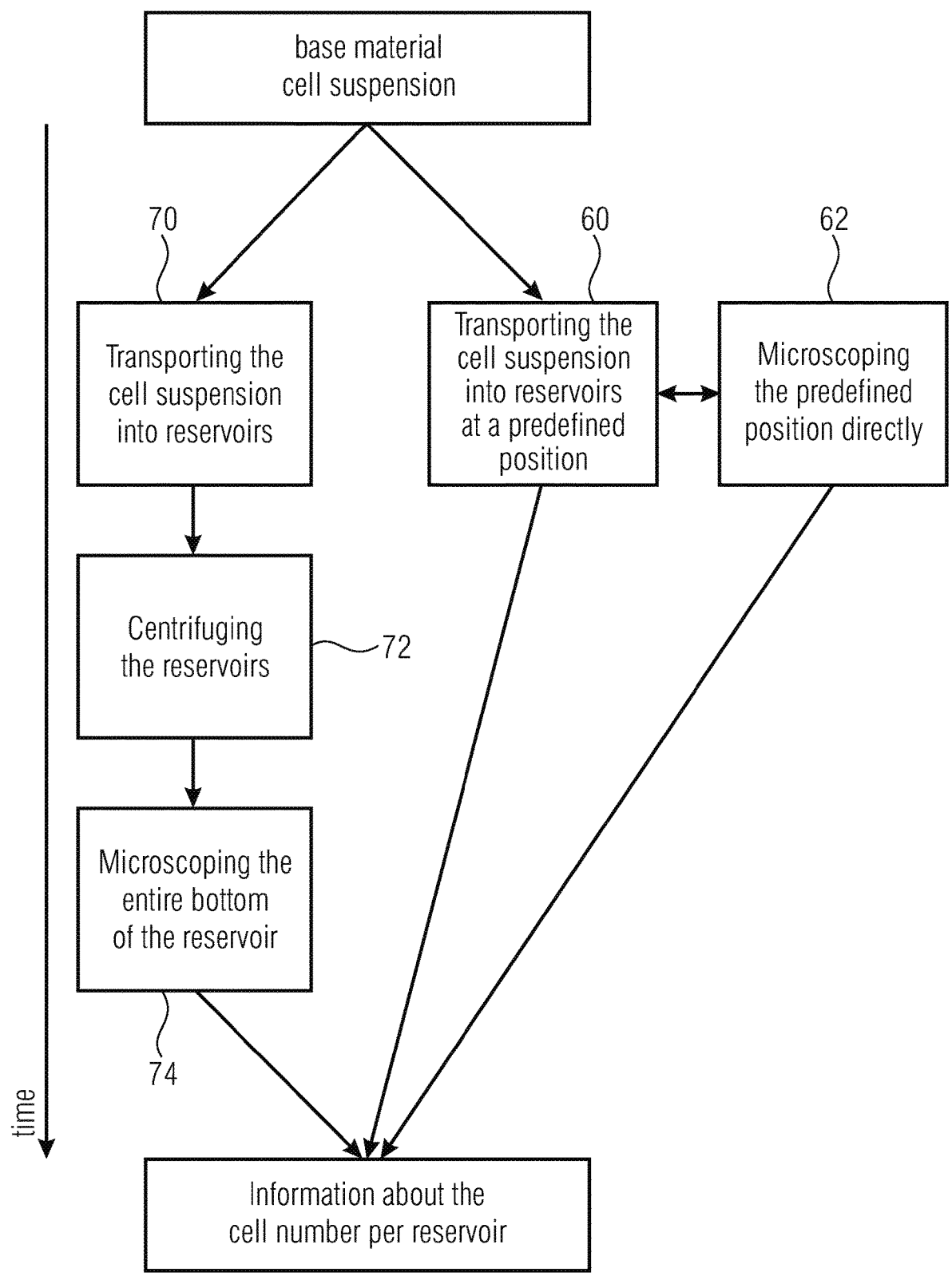
FIG. 5 shows a comparison of an embodiment of a method for detecting cells or particles in a fluid container described herein with a known method.

FIG. 5 illustrates a comparison of an embodiment described herein with a known method, the time axis being plotted from top to bottom. In each case, a cell suspension is used as the base material. In the method described herein, the cell suspension is transferred into reservoirs at a predefined position, step 60. Simultaneously, direct examination under a microscope of the predefined position occurs, step 62. As a result of steps 60 and 62, information about the cell count per reservoir is provided.

In contrast, in known methods, the cell suspension is transferred into reservoirs, step 70, the reservoirs are centrifuged, step 72, and examining the entire bottom of the reservoir under a microscope occurs, step 74. Thus, known methods comprise a significantly higher time expenditure, the height of the single process blocks in FIG. 5 being correlated with the duration of the corresponding steps. It has been found that a simplification and acceleration of the overall process is achieved by the methods described herein.

Hence, embodiments of the present invention enable an improved verification of single cells in a cell separation, while the entire process is simplified and accelerated. Simultaneously, the prerequisite remains that the cell may be dispensed into a sufficiently large volume enabling a subsequent cultivation (growth of the cells). Embodiments include a corresponding step of a cell cultivation in the fluid container after detecting a cell in the same.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A method for detecting cells or particles in a fluid container, comprising:
   dispensing at least one cell or at least one particle into a defined sub-volume of a fluid, wherein the fluid at least partially fills a fluid container, and wherein the defined sub-volume is directly underneath a surface of the fluid and extends downward by a predetermined depth from the surface of the fluid with which the fluid container is at least partially filled;
   performing, in a time-coordinated manner with dispensing the at least one cell or the at least one particle, a detection in the defined sub-volume and/or in one or several sub-volumes underneath the defined sub-volume in order to sense the at least one cell or the at least one particle when entering the fluid or no later than 10 seconds after entering the fluid.

2. The method according to claim 1, wherein the fluid is a liquid and the defined sub-volume comprises an area parallel to a liquid surface of the liquid in the fluid container, which is smaller than the area of an entry opening of the fluid container.

3. The method according to claim 1, wherein the at least one cell or the at least one particle is dispensed onto a surface of the fluid.

4. The method according to claim 3, wherein a detection of the at least one cell or the at least one particle is performed in the defined sub-volume comprising a depth of less than 5 mm from the upper surface of the fluid.

5. The method according to claim 1, wherein, starting with a sub-volume in a first depth, detections are successively performed in several sub-volumes comprising a respectively decreasing depth, or, starting with a sub-volume in a second depth, detections are successively performed in several sub-volumes comprising a respectively increasing depth.

6. The method according to claim 1, wherein performing a detection comprises focusing on the defined sub-volume and/or the one or several sub-volumes underneath the defined sub-volume and capturing images of the defined sub-volume and/or of the one or several sub-volumes underneath the defined sub-volume.

7. The method according to claim 6, wherein the fluid container is transparent and performing a detection occurs by means of an image capturing apparatus arranged underneath the fluid container.

8. The method according to claim 1, comprising positioning a dispenser, a detection apparatus and each one of several fluid containers relative to each other in order to sense the at least one cell or the at least one particle when entering the fluid or immediately after entering the fluid of each one of the several fluid containers.

* * * * *